United States Patent [19]

Murdoch

[11] 4,405,109
[45] Sep. 20, 1983

[54] PORTABLE BATHROOM HANGERS FOR HYGIENIC IRRIGATION EQUIPMENT

[76] Inventor: Merle A. Murdoch, Rte. #1, Box 194-K, Shelby, N.C. 28150

[21] Appl. No.: 300,045

[22] Filed: Sep. 8, 1981

[51] Int. Cl.³ .............................................. E04G 3/00
[52] U.S. Cl. .................................. 248/215; 248/311.2
[58] Field of Search ................... 248/311.3, 311.2, 214, 248/215, 309, 340; 228/227; 211/71, 113

[56] References Cited

U.S. PATENT DOCUMENTS

| 1,341,198 | 5/1920 | Ruple | 248/214 |
| 1,426,787 | 8/1922 | Spencer | 248/214 X |
| 2,487,645 | 11/1949 | Gershon | 248/214 UX |
| 3,127,114 | 3/1964 | Shaw | 248/214 X |
| 3,140,557 | 7/1964 | Albrycht | 248/340 |
| 3,384,231 | 5/1968 | Cox et al. | 248/340 X |
| 3,477,679 | 11/1969 | Lovitz | 248/309 |
| 3,664,626 | 5/1972 | Sneller | 248/214 X |
| 3,989,213 | 11/1976 | Allen | 248/214 |
| 4,036,368 | 7/1977 | Munsch | 248/226.4 X |
| 4,284,981 | 8/1981 | Black | 248/214 X |

Primary Examiner—J. Franklin Foss
Attorney, Agent, or Firm—Robert Brown, Jr.

[57] ABSTRACT

A portable bathroom accessory adapted to be detachably supported along the length of the lintel or head bar of a bath stall doorway while suspending many types of hygienic equipment such as syringe and stoma irrigation devices during use or for bathroom storage. Specifically, the invention is characterized by an inverted U-shaped hanger detachably and snugly mounted upon the head bar in a stable position, wherein one leg of the hanger serves the dual function of suspending a hygienic reservoir assembly in a partially stabilized position by limiting the swinging movement of the lower free end portion of the assembly backwardly in the direction of the other hanger leg. The hanger is further characterized by its light weight, compactness, mobility, resiliency and by its suitability for use in combination with a wide range of sizes and cross-sectional shapes of head bars, thereby enabling the user to conveniently include the hanger in his or her travel baggage with the assurance that it will fit the head bars of most bathroom stalls.

1 Claim, 5 Drawing Figures

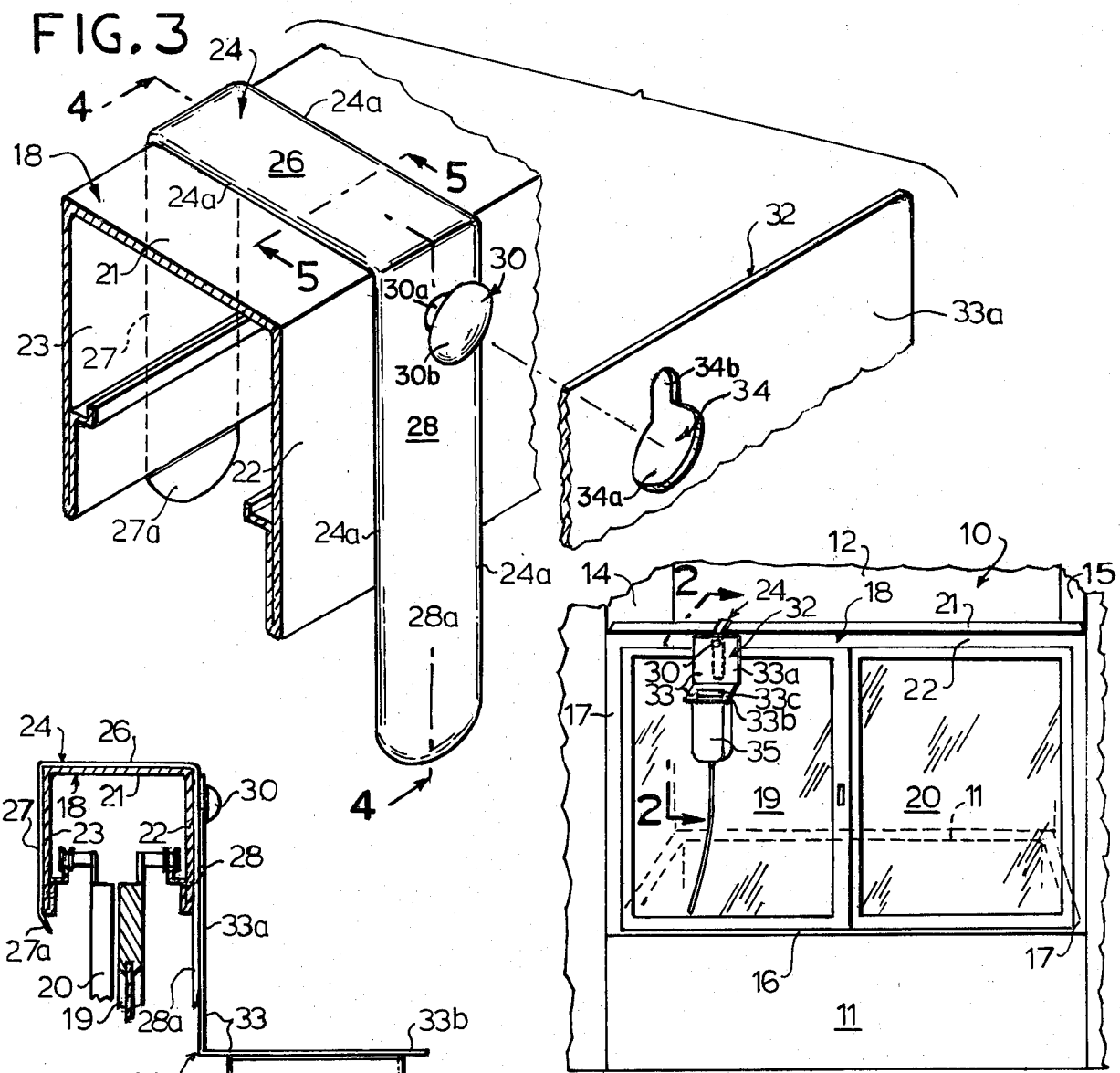

PORTABLE BATHROOM HANGERS FOR HYGIENIC IRRIGATION EQUIPMENT

The present invention relates to bathroom accessories and more especially to hangers for suspending stoma irrigation reservoirs and similar gravity-flow devices for irrigating body cavities.

It is a well-known fact that colostomy patients are provided with an artificial rectum, or stoma, in the abdomen wall of the body for elimination of waste from the colon. Since the stoma has no voluntary sphincter control, it is necessary for the patient to periodically irrigate through the stoma to prevent unintentional bowel movement, in a manner more fully described in U.S. Pat. Nos. 3,910,274 and 4,050,461. The stoma irrigation process, as well as similar types of enemas and douches, are generally carried out where bathroom facilities are available.

Heretofore, numerous types of hangers have been provided for suspending articles such as clothing, pictures, receptacles and various other mechanical devices. The patents to: Hochstrasser, No. 28,174; Wolke, No. 1,133,208; Casey, No. 2,024,429; Waddill, No. 2,507,842, and Constant, No. 3,131,812 are typical examples of such prior art suspension devices. None of the above-mentioned patents nor, so far as applicant is aware, any other prior art provide a portable hanger supported by the rail of a bath stall doorway and comprising an inverted U-shaped hook portion removably fitting over the rail and extending downwardly into the door opening, in combination with pivot means carried by the upper portion of the downwardly depending leg for swingably suspending an irrigation reservoir parallel to the plane of the opening, and with braking means for damping the movement.

It is therefore an object of this invention to provide a portable hanger for use on rails of bath stall doorways as set forth in the above abstract of the disclosure and specification characterized in the immediately preceding paragraph.

Some of the objects of invention having been stated, other objects will appear as the description proceeds when taken in connection with the accompanying drawings, in which, FIG. 1 is a front view of a bath stall of a bathroom, showing a hanger according to the present invention detachably mounted upon the head bar or rail of the stall doorway and with a hygienic irrigation device suspended from the hanger in the dressing area of the bathroom;

FIG. 2 is a vertical sectional view taken along line 2—2 in FIG. 1;

FIG. 3 is an exploded isometric view of the upper portion of FIG. 2;

FIG. 4 is a sectional detail view through the hanger when detached from the head bar, and taken along line 4—4 in FIG. 3;

FIG. 5 is a typical cross-sectional view of the detached hanger, and taken along line 5—5 in FIG. 3.

Referring more particularly to FIGS. 1-5 of the drawings the numeral 10 denotes a bath stall of a bathroom and comprising tub 11, back wall 12 and oppositely disposed side walls 14 and 15. The upper front wall of tub 11 cooperates with side walls 14 and 15 to form a the sill and jamb, respectively, of a front opening or doorway 16 to the stall. The upper area of the opening is spanned by a horizontally disposed rail 18 from which closure means such as doors or curtains 19 and 20 are slidably suspended.

Track members 18 has an inverted U-shaped cross-section throughout its length and consists of a top side 21 and front and rear sides 22 and 23 respectively. The space between the side walls 14 and 15 of stall 10 and above the track 18 normally remains open for purposes of ventilation. Applicant's hanger 24 is adpated to be detachably and firmly anchored mounted on track member or head bar 18 as hereinafter described in detail.

Hanger 24 has an inverted U-shape comprising top segment 26 and downwardly extending back and front segments 27 and 28 respectively, said segments 26, 27 and 28 being adapted to closely fit substantially in face-to-face contact with the top, back and front sides 21, 23 and 22 respectively of the track member 18 as shown in FIGS. 2 and 3. Preferably, the hanger is made from resilient, light-weight plastic or metallic material to cause the leg segments to normally clamp the opposite sides 22 and 23 of the track, but permitting the free end portions thereof to be spread apart during installation and removal of the hanger on and from the track. The lower end of the back leg segment 27 has integral therewith a short projection 27a which fits beneath the lower edge of track side 23 to releasably latch the hanger to the track.

It will be observed in FIGS. 1-3 that the segment 28 of the installed U-shaped hanger 24 depends vertically downwardly below rail or trackway 18 and adjacently parallel to a vertical plane containing trackway 18 and door opening 16; and, in turn, the irrigation device 32 is suspended from pivot means 30 alongside the flat depending leg or bar 28, 28a. More particularly, the pivot means 30 consists of a neck segment 30a extending perpendiculary fom the front face of bar 28, and of a knob 30b provided with an annular surface 30c surrounding the neck segment and parallel to the face of bar 28. The space between annular surface 30c and the proximate face of bar 28 is slightly more than the thickness of the vertical flange 33a described below in connection with irrigation device 32.

The device 32 comprises an L-shaped frame 33 having vertical and horizontal flanges 33a and 33b respectively, said vertical flange being provided with an inverted keyhole or bayonet slot 34 having open end 34a and a relatively narrow upper slotted end 34b. In order to pivotally suspend device 32 for oscillations substantially parallel to the plane of opening 16, the lower slot end 34a is laterally inserted over knob 30b, and then the flange 33a is lowered to insert the narrow slot end 34b over and upon restricted neck segment 30a, thereby supporting the flange 33a for oscillation between and face-to-face with annular surface 30c and the face of bar 28. The horizontal flange 33b has an opening 33c therein (FIG. 1), which opening coincides with the upper open end of a bag or container 35 suspended from the flange 33b. The perimeter or edges of U-shaped hanger 24 are rounded as at 24a to eliminate sharp edges which might cause injury to the user or damage to articles (FIGS. 4 & 5).

The bag or reservoir 35 is suspended from pivot means 30 in a cantilevered position normal to the plane of door opening 16 in addition to its previously described suspension parallel to the door plane, as shown in FIG. 2. In its cantilevered position the weight of the device 32, especially when bag 35 contains liquid, will bias clockwise rotation of frame 33 about knob 30b to cause vertical flange 33a to be laterally rotated into face-to-face frictional engagement with depending bar 28, 28a. This frictional interfacial engagement will damp the oscillation and swinging movement of the device about pivot means 30 and parallel to opening 16.

It is important to note that limited oscillation of device 32 is desirable when the patient receives an enema; however, the amplitude of oscillation must be damped to provide a reasonable amount of stability and rigidity at the point of suspension of the device.

The bottom of bag 35 has connected thereto a conventional flexible tube 36 of the type shown in the previously mentioned Constant U.S. Pat. No. 3,131,812, the lower end of the tube 36 being provided with a nozzle (not shown) but which is used for manual insertion in a body opening or stoma to perform an enema in a well known manner. During such a procedure, the tube and nozzle may be maneuvered at various distances and angles relative to reservoir or bag 35 thereby causing the lower free end of the device 32 to oscillate and swing about pivot means 30 in opposition to said damping action.

The manipulation of the tube and nozzle may also produce oscillation of the device about its vertical axis. The amplitude of such torsional movement will likewise be limited and damped by said interfacial connection between bar 28, 28a and flange 33a.

With the hanger 24 securely anchored to rail 18 and with a damped stabilized connection provided at pivot means 30, the oscillation, vibration and swinging movement of the lower free end of the suspended device 32 will be reduced within acceptable amplitudes during use.

I claim:

1. In a bath compartment having a door opening (16) spanned by an elevated horizontally disposed rail (18), a portable hygienic irrigation device (32) including a reservoir (35), and means carried by said rail for suspending said device comprising an inverted U-shaped hanger (24) detachably fixed to said rail;

one leg of said hanger consisting of a flat bar (28, 28a) depending adjacently parallel to the plane of said opening (16), said irrigation device (32) consisting of an L-shaped unitary frame having a flat vertically disposed flange (33a) and a horizontally disposed flange (33b);

pivot means (34a, 34b) for oscillatably suspending the vertical flange (33a) of said frame upon said pivot means (30) and face-to-face with said depending bar (28, 28a) to thereby suspend the device for oscillation parallel to the plane of said opening and means including said horizontal flange (33b) for cantilevering said reservoir (35) axially outwardly from said pivot means (30) and from the plane of said opening, said last-named means being responsive to a lateral stress component of the weight of said reservoir for biasing said vertical flange (33b) in face-to-face frictional engagement with said depending bar (28, 28a) whereby the amplitude of oscillation of said device is lessened.

* * * * *